US00PP33956P2

(12) United States Plant Patent
Masor

(10) Patent No.: US PP33,956 P2
(45) Date of Patent: Feb. 15, 2022

(54) ***ANGELONIA* PLANT NAMED 'BALADANUCB'**

(50) Latin Name: *Angelonia angustifolia*
Varietal Denomination: Baladanucb

(71) Applicant: Ball Horticultural Company, West Chicago, IL (US)

(72) Inventor: Laura L. Masor, Grover Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/501,573

(22) Filed: Oct. 14, 2021

(51) Int. Cl.
*A01H 6/68* (2018.01)
*A01H 5/02* (2018.01)

(52) U.S. Cl.
USPC ..... Plt./404

(58) Field of Classification Search
USPC ..... Plt./404
See application file for complete search history.

*Primary Examiner* — Annette H Para
(74) *Attorney, Agent, or Firm* — Audrey Charles

(57) ABSTRACT

A new and distinct cultivar of *Angelonia* plant named 'Baladanucb', characterized by its dark purplish-red and white bicolored, dark green-colored foliage, and moderately vigorous, upright growth habit, is disclosed.

1 Drawing Sheet

Latin name of genus and species of plant claimed: *Angelonia angustifolia.*

Variety denomination: 'Baladanucb'.

BACKGROUND OF THE INVENTION

The present invention relates to a new and distinct cultivar of *Angelonia* plant botanically known as *Angelonia angustifolia* and hereinafter referred to by the cultivar name 'Baladanucb'.

The new *Angelonia angustifolia* cultivar is a naturally-occurring sport of the proprietary *Angelonia angustifolia* breeding selection coded ANG-7123-04, not patented, characterized by its dark violet and white bicolored flowers, dark green-colored foliage, and vigorous, upright growth habit. The new cultivar was discovered as a side shoot and selected during May 2019 in a controlled environment in Arroyo Grande, Calif.

Asexual reproduction of the new cultivar by terminal stem cuttings since May 2019 in Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Baladanucb' as a new and distinct cultivar of *Angelonia* plant:

1. Dark purplish-red and white bicolored flowers;
2. Dark green-colored foliage; and
3. Moderately vigorous, upright growth habit.

Plants of the new cultivar differ from plants of the parent primarily in having dark purplish-red and white bicolored flowers and reduced growth vigor.

Of the many commercially available *Angelonia* cultivars, the most similar in comparison to the new cultivar is Archangel Blue Bicolor 'Balarclubi', not patented. However, in side-by-side comparisons, plants of the new cultivar differ from plants of 'Balarclubi' in at least the following characteristics:

1. Plants of the new cultivar are taller than plants of 'Balarclubi';
2. Plants of the new cultivar have a dark purplish-red and white bicolored flower color unlike plants of 'Balarclubi'; and
3. Plants of the new cultivar have a more pronounced white flower color than plants of 'Balarclubi'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Baladanucb'. The plants were approximately 4.5-months old. The plants were grown in 3-gallon containers for approximately 11 weeks in an outdoor nursery in West Chicago, Ill. Plants were pinched twice prior to transplant.

DETAILED BOTANICAL DESCRIPTION

Figure 1:
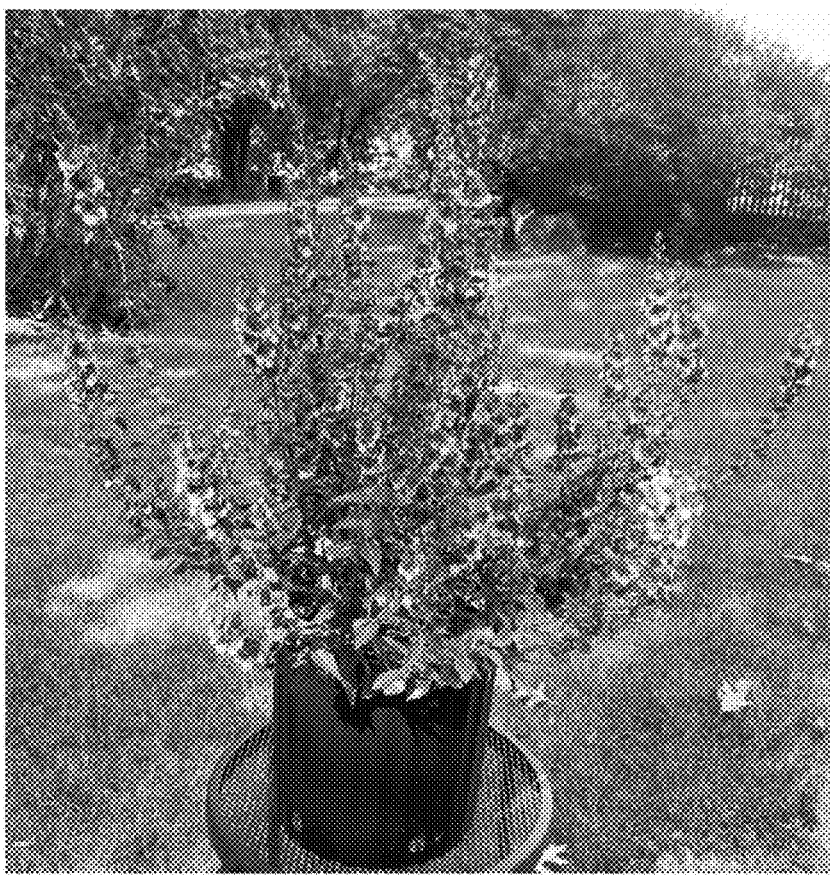
FIG. 1 illustrates a side view of the overall growth and flowering habit of 'Baladanucb'.
Figure 2:
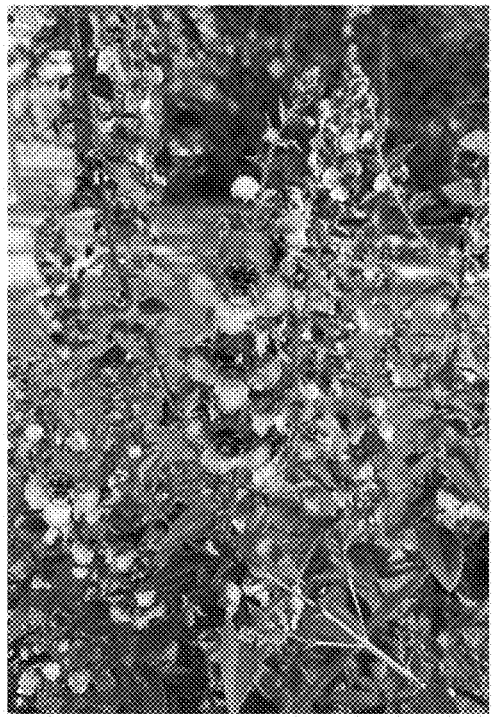
FIG. 2 illustrates a close-up view of an individual inflorescence of 'Baladanucb'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in August 2021 under natural light conditions in Naperville, Ill.

The following descriptions and measurements describe approximately 4.5-month-old plants produced from cuttings from stock plants and grown under conditions comparable to those used in commercial practice. The plants were grown in 3-gallon containers for approximately 11 weeks in an outdoor nursery in West Chicago, Ill. Plants were given two pinches prior to transplant. Prior to transplant plants were grown in a polycarbonate greenhouse in West Chicago, Ill. Greenhouse temperatures were maintained at approximately 70° F. to 85° F. (21° C. to 29° C.) during the day and approximately 60° F. to 70° F. (16° C. to 21° C.) during the night. Supplemental lighting was used during propagation stage. Measurements and numerical values represent averages of typical plants.

Botanical classification: *Angelonia angustifolia* 'Baladanucb'.

Parentage:

*Parent*.—Proprietary *Angelonia angustifolia* breeding selection coded ANG-7123-04, not patented, not patented.

Propagation:

*Type cutting*.—Terminal stem.

*Time to initiate roots*.—Approximately 7 to 9 days.

*Time to produce a rooted cutting*.—Approximately 21 to 28 days.

*Root description*.—Fine, fibrous.

*Rooting habit*.—Freely branching.

Plant description:

*Commercial crop time*.—Approximately 5 to 8 weeks from a rooted cutting to finish in a 10 cm pot.

*Growth habit and general appearance*.—Moderately vigorous, upright.

*Size*.—Height from soil level to top of plant plane: Approximately 73.0 cm. Width: Approximately 67.0 cm.

*Branching habit*.—Freely branching, pinching improves basal branching. Quantity of main branches per plant: Approximately 7.

*Branch*.—Shape: Square in cross section. Strength: Moderately strong. Length: Approximately 38.0 cm. Diameter: Approximately 4.0 mm to 7.0 mm. Length of central internode: Approximately 1.7 cm. Texture: Glabrous. Color of young and mature stems: 144B.

Foliage description:

*General description*.—Quantity of leaves per main branch: Approximately 18. Fragrance: None. Form: Simple. Arrangement: Opposite.

*Leaves*.—Aspect: Primarily perpendicular or obtuse angle to stem. Shape: Elliptic. Margin: Widely serrate. Apex: Acute. Base: Sessile. Venation pattern: Pinnate. Length of mature leaf: Approximately 5.3 cm. Width of mature leaf: Approximately 2.0 cm. Texture of upper and lower surfaces: Sparsely glandular pubescent. Gland color: Colorless, transparent. Color of upper surface of young and mature foliage: NN137A with midvein of 146C and other venation indistinguishable. Color of lower surface of young and mature foliage: Closest to 146A with midvein of 146C and other venation indistinguishable.

Flowering description:

*Flowering habit*.—'Baladanucb' is freely flowering under outdoor growing conditions with substantially continuous blooming from spring through autumn and year-round in greenhouse environment.

*Lastingness of individual flower on the plant*.—Approximately 7 to 10 days.

Inflorescence description:

*General description*.—Type: Terminal raceme. Quantity per plant: Approximately 55. Fragrance: Slight, sweet. Length: Approximately 30.0 cm. Width: Approximately 3.0 cm to 4.0 cm. Quantity of fully open flowers per inflorescence: Approximately 5 to 9.

Flower description:

*Type*.—Solitary, zygomorphic.

*Bud*.—Rate of opening: Generally takes 3 to 4 days for bud to progress from first color to fully open flower.

*Bud just before opening*.—Shape: Globular. Diameter: Approximately 6.0 mm. Color of upper surface: 145B. Color of lower surface: 144A.

*Corolla*.—Shape: Bilabiate. Aspect: Facing outward. Length: Approximately 2.7 cm. Width: Approximately 2.3 cm. Depth: Approximately 9.0 mm.

*Petals*.—Quantity: 5 petals fused at base forming a throat and consisting of an upper lip with 2 petals and a lower lip with 3 petals, consisting of 2 lateral petals and one central petal. Shape: Obovate. Margin: Entire, wavy. Apex: Obtuse.

*Upper lip*.—Length of petals from throat: Approximately 8.0 mm. Width of each petal: Approximately 1.2 cm. Texture of upper surface: Densely glandular pubescent. Gland color: 150C and colorless, transparent. Texture of lower surface: Sparsely glandular pubescent. Gland color: Colorless, transparent. Color of upper surface when fully open: 72A to 72B. Color of lower surface when fully open: 72B.

*Lower lip, lateral petals*.—Length of petals from throat: Approximately 1.0 cm. Width of each petal: Approximately 1.3 cm. Texture of upper and lower surfaces: Densely glandular pubescent. Gland color: 150C and colorless, transparent. Color of upper surface when fully open: NN155A mottled with 72A, patch of 72A to 72B on approximately one quarter of area nearest upper petals, margins of 72B adjacent to NN155A. Color of lower surface when fully open: 155A with 72B on approximately one quarter of area nearest upper petals, margins of 72B.

*Lower lip, central petal*.—Length from the palate: Approximately 9.0 mm. Width: Approximately 1.0 cm. Texture of upper and lower surfaces: Densely glandular pubescent. Gland color: 150C and colorless, transparent. Color of upper surface when fully open: NN155A mottled with 72A and margins of 72B. Color of lower surface when fully open: 155A with margins of 72B.

*Throat*.—Length: Approximately 9.0 mm. Width: Approximately: 6.0 mm. Texture of inner and outer surfaces: Sparsely glandular pubescent. Gland color: 150C, transparent. Color of inner surface: NN155D with a faint overlay of 72B and spots of N79A. Color of outer surface: 155A with a faint overlay of 72B and spots of N79A. Palate color: 72B, 137A, and 144A with spots of N79A, lower lip of NN155A mottled with 72B. Palate texture: Sparsely glandular pubescent. Gland color: 150C, transparent. Teeth color: 155A with 72B.

*Calyx*.—Shape: Star, cupped. Diameter: Approximately 6.0 mm.

*Sepals*.—Quantity per flower: 5, fused at base. Shape: Ovate. Apex: Acute. Length: Approximately 3.0 mm. Width: Approximately 2.0 mm. Texture of upper (inner) surface: Sparsely glandular pubescent. Texture of lower (outer) surface: Densely glandular pubescent. Gland color: 150C and colorless, transparent. Color of upper (inner) surface: 137A. Color of lower (outer) surface: 137A with an overlay of 187A.

*Pedicel*.—Strength: Strong, flexible. Aspect: Acute angle to stem. Length: Approximately 9.0 mm. Diameter: Approximately 1.0 mm. Texture: Sparsely glandular pubescent. Gland color: Colorless, transparent. Color: 146B with an overlay of 187A.

*Reproductive organs*.—Androecium: Stamen quantity: 4 per flower. Filament length: Approximately 4.0 mm. Filament texture: Sparsely glandular pubescent. Gland color: Colorless, transparent. Filament color: NN155D faintly tinted with 72A. Anther shape: Bilobed. Anther length: Approximately 1.0 mm. Anther color: 72A. Pollen amount: Abundant. Pollen color: 155D. Gynoecium: Pistil quantity: 1 per flower. Pistil length: Approximately 4.0 mm. Stigma shape: Pointed. Stigma length: Less than 1.0 mm. Stigma color: NN155D. Style length: Approximately 3.0 mm. Style color: NN155D. Ovary diameter: Approximately 1.0 mm. Ovary texture: Sparsely glandular pubescent. Gland color: 150C, transparent. Ovary color: 146D.

Seed and fruit production: Neither seed nor fruit production has been observed.

Disease and pest resistance: Resistance to pathogens and pests common to *Angelonia* has not been observed.

What is claimed is:

1. A new and distinct cultivar of *Angelonia* plant named 'Baladanucb', substantially as herein illustrated and described.

* * * * *